US006803190B1

(12) United States Patent
Rothschild et al.

(10) Patent No.: US 6,803,190 B1
(45) Date of Patent: Oct. 12, 2004

(54) MELANOCORTIN-4 RECEPTOR GENE AND USE AS A GENETIC MARKER FOR FAT CONTENT, WEIGHT GAIN, AND/OR FEED CONSUMPTION OF ANIMALS

(75) Inventors: Max F. Rothschild, Ames, IA (US); Kwan Suk Kim, Ames, IA (US); Niels J. Larson, Copenhagen (DK)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

(21) Appl. No.: 09/380,419

(22) PCT Filed: Jul. 26, 1999

(86) PCT No.: PCT/US99/16862

§ 371 (c)(1),
(2), (4) Date: Jul. 24, 2000

(87) PCT Pub. No.: WO00/06777

PCT Pub. Date: Feb. 10, 2000

Related U.S. Application Data

(60) Provisional application No. 60/116,186, filed on Jan. 15, 1999, and provisional application No. 60/094,287, filed on Jul. 27, 1998.

(51) Int. Cl.[7] .................................................. C12Q 1/68
(52) U.S. Cl. ........................ 435/6; 435/91.2; 536/23.1; 536/23.4; 536/24.32; 536/24.3
(58) Field of Search .................. 435/6, 91.2; 536/24.3, 536/24.32, 23.4, 23.1

(56) References Cited

U.S. PATENT DOCUMENTS 5,547,843 A * 8/1996 Studier et al. .................. 435/6
5,595,874 A * 1/1997 Hogan et al. .................. 435/6
5,614,364 A * 3/1997 Tuggle et al. .................. 435/6
5,703,220 A * 12/1997 Yamada et al. ............ 536/23.5

FOREIGN PATENT DOCUMENTS

WO  WO 97 23644 A   7/1997   ............ C12Q/1/68
WO  WO 97 47316 A   12/1997  ............ C12Q/1/68
WO  WO 00/06777     2/2000

OTHER PUBLICATIONS

Yeo et al. Oct. 1998. Nature Genetics. vol. 20. 111–112.*
Boehringer Mannheimm 1997 Biochemicals Catalog. p. 122.*
Stratagene Catalog. 1988. p. 39.*
Kim K., et al., "A missense variant of the porcine melanocortin–4 receptor (MC4R) gene is associated with fatness, growth and feed intake traits", *Mammalian Genome*, vol. 11, No. 2, (2000–02), pp. 131–135 XP002944421.
Nezer C. et al., "An imprinted QLT with major effect on muscle mass and fat deposition maps to the IGF2 locus in pigs", *Nature Genetics*, vol. 21, No. 2 (1999–02) pp. 155–156 XP002204960.
Andersson, L., et al., "Genetic Mapping of quantitative trait loci for growth and fatness in pigs", *Science*, 263:1771–1774.
Gotoda, T., "Molecular screening of the human melanocortin–r receptor gene: identification of a missense variant showing no association with obesity, plasma glucose, or insulin", *Diabetologia* 40:976–979 (1997).

* cited by examiner

Primary Examiner—Jeffrey Fredman
Assistant Examiner—Juliet C. Switzer
(74) Attorney, Agent, or Firm—McKee, Voorhees & Sease, P.L.C.

(57) ABSTRACT

Genetic markers in the Porcine melanocortin-4 receptor (MC4R) gene are disclosed which are associated with fat content, growth rate, and feed consumption. Further, novel sequence data from regions of the gene are disclosed which may be used in a PCR test to screen for the presence of the marker. The genetic marker may be used to screen animals for breeding purposes which have the desired traits regarding fat content, growth rate, and feed consumption. Kits which take advantage of the PCR test are also disclosed.

11 Claims, 14 Drawing Sheets

```
  1  ACAAGAATCT GCATTCACCC ATGTACTTTT TCATCTGTAG CCTGGCTGTG
 51  GCTGATATGC TGGTGAGCGT TTCCAATGGG TCAGAAACCA TTGTCATCAC
101  CCTATTAAAC AGCACGGACA CGGACGCACA GAGTTTCACA GTGAATATTG
151  ATAATGTCAT TGACTCAGTG ATCTGTAGCT CCTTACTCGC CTCAATTTGC
201  AGCCTGCTTT CGATTGCAGT GGACAGGTAT TTTACTATCT TTTATGTCT
251  CCAGTACCAT AACATTATGA CAGTTAAGCG GGTTGGAATC ATCATCAGTT
301  GTATCTGGGC AGTCTGCACG GTGTCGGGTG TTTTGTTCAT CATTACTCA
351  GATAGCAGTG CTGTTATTAT CTGCCTCATA ACCGTGTTCT TCACCATGCT
401  GGCTCTCATG GCTTCTCTCT ATGTCCACAT GTTCCTCATG GCCAGACTCC
451  ACATTAAGAG GATCGCCGTC CTCCCAGGCA CTGGCACCAT CCGCCAAGGT
501  GCCAACATGA AGGGGGCAAT TACCCTGACC ATCTTGATTG GGGTCTTTGT
551  GGTCTGCTGG GCCCCCTTCT TCCTCCACTT AATATTCTAT ATCTCCTGCC
```

*Fig. 1*

601 CCCAGAATCC ATACTGTGTG TGCTTCATGT CTCACTTTAA TTTGTATCTC
651 ATCCTGATCA TGTGTAATTC CATCATCKAT CCCCTGATTT ATGCACTCCG
701 GAGCCAAGAA CTGAGGAAAA CCTTCAAAGA GATCATCTGT TGCTAT

Fig. 1A

```
con-mc4r.seq                    ACAAGAATCTGCATTCACCCATGTACTTTT
                                ||||||||||||||||||||||||||||||
877415       ATATCTTAGTGATTGTGGCAATAGCCAAGAACAAGAATCTGCATTCACCCATGTACTTTT
             580       590       600       610       620       630 con-mc4r.seq TCATCTGTAGCCTGGCTGTGGCTGATATGCTGGTGAGCGTTTCCAATGGTCAGAAAACCA
             |||||||| ||||||||||||||||||||||||||||||||||||| ||||||||||||
877415       TCATCTGCAGCTTGGCTGTGGCTGATATGCTGTGTGAGCCGTTTCAAATGGATCAGAAACCA
             640       650       660       670       680       690 con-mc4r.seq TTGTCATCATCCCTATTATTAAACAGCACGGACACGGAGTTTCACAGTGAATATATTG
             || |||||||||||||||||||||||| ||||||||||||||||||||||||||||||
877415       TTATCATCATCCCTATTATTAAACAGTACAGTAGATACAGATACAGAGTTTCACAGTGAATATATTG
             700       710       720       730       740       750 con-mc4r.seq ATAATGTCATTGACTCAGTGATCGTGATCGCTTCCTTACTCGCCTCAATTTGCAGCCTGCTTT
             |||||||||||||||| ||||||||||||| ||||||||||||||| ||||||||||||
877415       ATAATGTCATTGACTCGGGTGATCGTGATCGTAGCTCCTTGCTTGCATCCATTTGCAGCCTGCTTT
             760       770       780       790       800       810
```

*Fig. 2A*

```
con-mc4r.seq  CGATTGCAGTGGACAGGTATTTTACTATCTTTATGCTCTCCAGTACCATAACATTATGA
                 220       230       240       250       260       270
              ||||||||||||||||||||||||||||||||||||||||||||||||||||||||||||
              CAATTGCAGTGGACAGGTACTTTACTATCTTTACTATCTTCCAGTACCATAACATTATGA
877415          820       830       840       850       860       870 con-mc4r.seq  CAGTTAAGCGGGTTGGAATCATCATCAGTCAGTTGTATCTGGGCAGTCTGCACGGTGTCGGGTG
                 280       290       300       310       320       330
              ||||||||||||||||||||||||||||||||||||||||||||||||||||||||||||
              CAGTTAAGCGGGTTGGGATCAGCATAAGTTGTATCTGGGCAGCTGCACGGTTTCAGGCA
877415          880       890       900       910       920       930 con-mc4r.seq  TTTTGTTCATCATTACTCAGATAGCAGTGCTGTTATTATCTGCCTCATAACCGTGTTCT
                 340       350       360       370       380       390
              ||||||||||||||||||||||||||||||||||||||||||||||||||||||||||||
              TTTTGTTCATCATTACTCAGATAGTAGTGCTGTCATCATCTGCCTCATCACCATGTTCT
877415          940       950       960       970       980       990 con-mc4r.seq  TCACCATGCTGGCTCTCATGGCTTCTCTATGTCCTCACATGTTCCTCATGGCCAGACTCC
                 400       410       420       430       440       450
              ||||||||||||||||||||||||||||||||||||||||||||||||||||||||||||
              TCACCATGCTGGCTCTCATGGCTTCTCTATGTCCTCATGTCCACATGTTCCTGATGGCCAGGCTTC
877415         1000      1010      1020      1030      1040      1050 con-mc4r.seq  ACATTAAGAGGATCGCCGTCCTCCCAGGCACTGGCACCATCCGGCCAAGGTGCCAACATGA
                 460       470       480       490       500       510
              ||||||||||||||||||||||||||||||||||||||||||||||||||||||||||||
              ACATTAAGAGGATTGCTGTCCTCCCCGGCACTGGTGCCATCCGGCCAAGGTGCCAATATGA
877415         1060      1070      1080      1090      1100      1110
```

Fig. 2B

```
con-mc4r.seq  AGGGGGCAATTACCCTGACCATCTTGATTGGGGTCTTTGTTGTGTCTGCTGGGCCCCTTCT
                    520       530       540       550       560       570
              |||||||||||||||||||||||||||||||||||||||||||||||||||||||| ||||
              AGGGAGCGATTACCTTGACCATCCTGATTGGCGTCTTTGTTGTCTGCTGGGCCCATTCT
s77415              1120      1130      1140      1150      1160      1170 con-mc4r.seq  TCCTCCACTTAATATTCTATATCTCCCCCCCCAGAATCCATACTGTGTGTGCTTCATGT
                    580       590       600       610       620       630
              |||||||||||||||||||||||||||||| |||||||||||||||||||||||||||||
              TCCTCCACTTAATATTCTACATCTCTGTCCTCAGAATCCATATTGTGTGTGCTTCATGT
s77415              1180      1190      1200      1210      1220      1230 con-mc4r.seq  CTCACTTTAATTTGTATCTCATCCTGATCATGTGTAATTCCATCATCAATCCCCTGATTT
                    640       650       660       670       680       690
              |||||||||||||||||||||||||||||||||||||||||||||||| ||||| |||||
              CTCACTTTAACTTGTATCTCATAGATCATGTGTAATTCATCATGTGATCATCCTCTGATTT
s77415              1240      1250      1260      1270      1280      1290 con-mc4r.seq  ATGCACTCCGGAGCTCCAAGAACTGAGGAAACCTTCAAAGAGATCATCTGTTGCTAT
                    700       710       720       730       740
              ||||||||||||||||||||||||||||||||||||||||||||||||||||| ||||||
              ATGCACTCCGGAGTCAAGAGAACTGAGGAAAAACCTTCAAAGAGATCATCTGTTGCTATCCCC
s77415              1300      1310      1320      1330      1340      1350

TGGGAGGCCTTTGTGACTTGTCTAGCAGATATTAAATGGGGACAGAGAGCACGCAATATAGG
s77415              1360      1370      1380      1390      1400      1410
```

*Fig. 2C*

```
human.pep     QLFVSPEVFVTLGVISLLENILVIVAIAKNKNLHSPMYFFICSLAVADMLVSVSNGSETI
                                         |||||||||||||||||||||||||||||||
mc4r-allel                                KNLHSPMYFFICSLAVADMLVSVSNGSETI
              50        60        70        80        90       100
                                           10        20        30 human.pep     IITLLNSTDTDAQSFTVNIDNVIDSVICSSLLASICSLLSIAVDRYFTIFYALQYHNIMT
              ||:|||||||||||||||||||||||||||||||||||||||||||||||||||||||||
mc4r-allel    VITLLNSTDTDAQSFTVNIDNVIDSVICSSLLASICSLLSIAVDRYFTIFYALQYHNIMT
              110       120       130       140       150       160
                    40        50        60        70        80        90 human.pep     VKRVGISISCIWAACTVSGILFIIYSDSSAVIICLITMFFTMLALMASLYVHMFLMARLH
              |||||| ||||||||:|||||||||||||||||||||||||||||||||||||||||||
mc4r-allel    VKRVGIIISCIWAVCTVSGVLFIIYSDSSAVIICLITVFFTMLALMASLYVHMFLMARLH
              170       180       190       200       210       220
                   100       110       120       130       140       150 human.pep     IKRIAVLPGTGAIRQGANMKGAITLTLIGVFVVCWAPFFLHLIFYISCPQNPYCVCFMS
              |||||||||||:|||||||||||||||||||||||||||||||||||||||||||||||
mc4r-allel    IKRIAVLPGTGTIRQGANMKGAITLTLIGVFVVCWAPFFLHLIFYISCPQNPYCVCFMS
              230       240       250       260       270       280
                   160       170       180       190       200       210 human.pep     HFNLYLILIMCNSIIDPLIYALRSQELRKTFKEIICCYPLGGLCDLSSRY
              ||||||||||||||||||||||||||||||||||||||||||
mc4r-allel    HFNLYLILIMCNSIIDPLIYALRSQELRKTFKEIICCY
              290       300       310       320       330
                   220       230       240
```

*Fig. 3A*

```
                    50        60        70        80        90       100
human.pep    QLFVSPEVFVTLGVISLLENILVTVAIARNKNLHSPMYFFICSLAVADMLVSVSNGSETI
                                        ||||||||||||||||||||||||||||||
mc4r-alle2                              KNLHSPMYFFICSLAVADMLVSVSNGSETI
                                                 10        20        30

110       120       130       140       150       160
human.pep    IITLLNSTDTDAQSFTVNIDNVIDSVICSSLLASICSLLSIAVDRYFTIFYALQYHNIMT
             :||||||||||||||||||| |||||||||||||||||||||||||||||||||||||||
mc4r-alle2   VITLLNSTDTDAQSFTVNIDNVIDSVICSSLLASICSLLSIAVDRYFTIFYALQYHNIMT
                   40        50        60        70        80        90

170       180       190       200       210       220
human.pep    VKRVGISISCIWAACTVSGILFIIYSDSSAVIICLITMFFTMLALMASLYVHMFLMARLH
             |||||  |||||| |||||||||||||||||||||||||||:||||||||||||||||||
mc4r-alle2   VKRVGIIISCIWAVCTVSGVLFIIYSDSSAVIICLITVFFTMLALMASLYVHMFLMARLH
                  100       110       120       130       140       150

230       240       250       260       270       280
human.pep    IKRIAVLPGTGAIRQGANMKGAITLTLIGVFVVCWAPFFLHLIFYISCPQNPYCVCFMS
             ||||||||||| |||||||||||||||||||||||||||||||||||||||||||||||
mc4r-alle2   IKRIAVLPGTGTIRQGANMKGAITLTLIGVFVVCWAPFFLHLIFYISCPQNPYCVCFMS
                  160       170       180       190       200       210

290       300       310       320       330
human.pep    HFNLYLILIMCNSIIDPLIYALRSQELRKTFKEIICCYPLGGLCDLSSRY
             |||||||||||||||:|||||||||||||||||||||||
mc4r-alle2   HFNLYLILIMCNSIINPLIYALRSQELRKTFKEIICCY
                  220       230       240
```

*Fig. 3B*

| | | | | | | |
|---|---|---|---|---|---|---|
| S0082 | MC4R | rec. fracs.= | 0.05, | lods | = | 14.74 |
| CGA | MC4R | rec. fracs.= | 0.14, | lods | = | 6.88 |
| S0020 | MC4R | rec. fracs.= | 0.18, | lods | = | 5.32 |
| S0079 | MC4R | rec. fracs.= | 0.12, | lods | = | 10.35 |
| S0155 | MC4R | rec. fracs.= | 0.14, | lods | = | 7.68 |
| S0122 | MC4R | rec. fracs.= | 0.18, | lods | = | 5.17 |
| S0313 | MC4R | rec. fracs.= | 0.00, | lods | = | 17.76 |
| S0312 | MC4R | rec. fracs.= | 0.20, | lods | = | 5.60 |
| S0311 | MC4R | rec. fracs.= | 0.17, | lods | = | 7.18 |
| S0416 | MC4R | rec. fracs.= | 0.20, | lods | = | 3.21 |
| S0331 | MC4R | rec. fracs.= | 0.02, | lods | = | 21.91 |
| S0396 | MC4R | rec. fracs.= | 0.16, | lods | = | 7.85 |
| BHT0433 | MC4R | rec. fracs.= | 0.02, | lods | = | 21.32 |
| S0536 | MC4R | rec. fracs.= | 0.03, | lods | = | 15.61 |
| CAPN3 | MC4R | rec. fracs.= | 0.12, | lods | = | 6.65 |

*Fig. 4A*

| | | | | | |
|---|---|---|---|---|---|
| KGF | MC4R | rec. fracs.= | 0.09, | lods = | 6.46 |
| MEF2A | MC4R | rec. fracs.= | 0.05, | lods = | 14.36 |
| MC4R | MC4R | rec. fracs.= | 0.00, | lods = | 26.19 |
| S0082 | MC4R | rec. fracs.= | 0.00, | 0.09, | lods = 15.86 |
| CGA | MC4R | rec. fracs.= | 0.07, | 0.22, | lods = 7.46 |
| S0020 | MC4R | rec. fracs.= | 0.00, | 0.25, | lods = 6.33 |
| S0079 | MC4R | rec. fracs.= | 0.00, | 0.19, | lods = 11.48 |
| S0155 | MC4R | rec. fracs.= | 0.00, | 0.24, | lods = 9.98 |
| S0122 | MC4R | rec. fracs.= | 0.00, | 0.27, | lods = 7.10 |
| S0313 | MC4R | rec. fracs.= | 0.00, | 0.00, | lods = 17.76 |
| S0312 | MC4R | rec. fracs.= | 0.04, | 0.29, | lods = 7.45 |

Fig. 4B

| | | | |
|---|---|---|---|
| S0311 MC4R rec. fracs.= | 0.00 | 0.28, | lods = 9.02 |
| S0416 MC4R rec. fracs.= | 0.00 | 0.31, | lods = 4.17 |
| S0331 MC4R rec. fracs.= | 0.05 | 0.00, | lods = 22.14 |
| S0396 MC4R rec. fracs.= | 0.03 | 0.24, | lods = 9.33 |
| BHT0385 MC4R rec. fracs.= | 0.14 | 0.36, | lods = 3.46 |
| BHT0433 MC4R rec. fracs.= | 0.05 | 0.00, | lods = 21.82 |
| S0536 MC4R rec. fracs.= | 0.00 | 0.05, | lods = 15.77 |
| CAPN3 MC4R rec. fracs.= | 0.00 | 0.18, | lods = 7.35 |
| KGF MC4R rec. fracs.= | 0.00 | 0.17, | lods = 6.74 |
| MEF2A MC4R rec. fracs.= | 0.10 | 0.00, | lods = 14.52 |
| MC4R MC4R rec. fracs.= | 0.00 | 0.00, | lods = 26.19 |

Fig. 4C

| | | | | |
|---|---|---|---|---|
| 0 | ESR | | | 0.0 |
| | | 0.18 | 18.4 | |
| 1 | S0008 | | | 18.4 |
| | | 0.12 | 11.9 | |
| 7 | CGA | | | 30.3 |
| | | 0.03 | 2.8 | |
| 3 | S0312 | | | 33.1 |
| | | 0.05 | 4.9 | |
| 4 | S0122 | | | 38.1 |
| | | 0.09 | 9.4 | |
| 8 | KGF | | | 47.4 |
| | | 0.06 | 5.8 | |
| 6 | CAPN3 | | | 53.2 |
| | | 0.02 | 2.5 | |
| 9 | MEF2A | | | 55.7 |
| | | 0.06 | 6.1 | |
| 5 | MC4R | | | 61.8 |
| | | 0.06 | 5.6 | |
| 10 | S0313 | | | 67.4 |
| | | 0.00 | 0.0 | |
| 11 | S0082 | | | 67.4 |
| | | 0.03 | 3.4 | |
| 12 | S0079 | | | 70.8 |
| | | 0.03 | 2.5 | |
| 14 | S0142 | | | 73.3 |
| | | 0.01 | 1.0 | |
| 13 | S0020 | | | 74.4 |
| | | 0.04 | 4.3 | |
| 15 | S0311 | | | 78.7 |
| | | 0.00 | 0.0 | |
| 16 | S0155 | | | 78.7 |
| | | 0.12 | 12.2 | |
| 17 | S0113 | | | 90.9 |
| | | 0.20 | 21.0 | |
| 18 | S0302 | | | 111.9 |
| | | 0.22 | 23.4 | |
| 19 | S0112 | | | 135.3 |

*Fig. 4D*

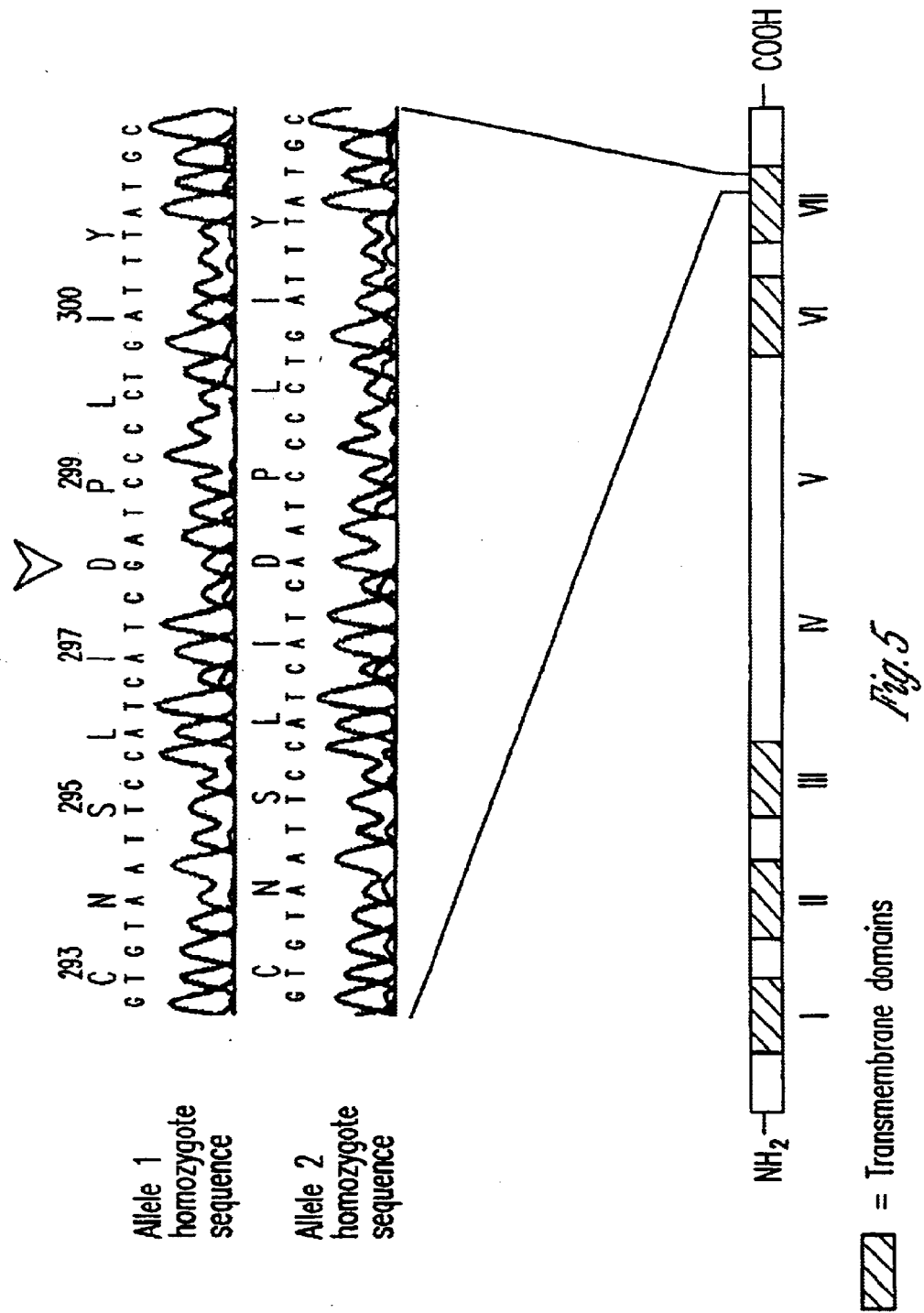

| | | |
|---|---|---|
| pMC4R | ......MSHFNLYLILIMCNSIIDPLIYAL...... | * |
| hMC4R | ......MSHFNLYLILIMCNSIIDPLIYAL...... | 304 |
| rMC4R | ......MSHFNLYLILIMCNAVIDPLIYAL...... | 304 |
| sheep MC5R | ......MSHFNMYLILIMCNSVIDPLIYA........ | 286 |
| bovine MC5R | ......MSHFNMYLILIMCNSVIDPLIYA........ | 286 |
| bovine MC2R | ......MSLFQVNGVLIMCNAIIDPFIYAL...... | 268 |
| hMC3R | ........AHFNTYLVLIMCNSVIDPLIYA........ | 327 |
| mMC3R | ........AHFNTYLVLIMCNSVIDPLIYA........ | 290 |
| hMC2R | ......MSHFNMYLILIMCNSVMDPLIYA........ | 268 |
| hMC1R | ........SYFNLFLILIICNSVVDPLIYA........ | 299 |
| bEDG-2R | ......LAYEKFFLLLAEFNSAMNPIIYSYR.... | 314 |
| hEDG-4R | ................FLLLAEANSLVNAAVYSCR.... | 298 |
| human cannab | ............VFAFCSMLCLLNSTVNPLIYAL...... | 399 |
| hH2AB | .............FQFFFWIGYCNSSLNPVIYTI...... | 290 |
| rSSR2 | .............FDFVVILTYANSCANPILYAFL.... | 315 |
| hGAL1-R | ....................LAYSNSSVNPIIYAFL.... | 306 |

*Fig. 7*

MELANOCORTIN-4 RECEPTOR GENE AND USE AS A GENETIC MARKER FOR FAT CONTENT, WEIGHT GAIN, AND/OR FEED CONSUMPTION OF ANIMALS

CROSS-REFERENCE TO RELATED APPLICATIONS

This application claims the benefit of U.S. Provisional Application Serial No. 60/094,287 filed Jul. 27, 1998 and U.S. Provisional Application Serial No. 60/116,186, filed Jan. 15, 1999, the disclosures of which are hereby incorporated by reference.

GRANT REFERENCE CLAUSE

This invention was supported at least in part by grants from the United States Department of Agriculture through the Iowa Agriculture and Home Economics Experiment Station (IaHees) and Project Number IOW03148 (Hatch Funds). The United States government may have certain rights in this invention.

FIELD OF THE INVENTION

The present invention relates to a method of genetically evaluating animals by assaying for the presence of at least one genetic marker which is indicative of one or more of the traits of fat content, growth rate, and feed consumption. In particular, the method analyzes for variation in the melanocortin-4 receptor (MC4R) gene which is indicative of these traits. Even more particularly, the method analyzes for a polymorphism in the MC4R gene.

BACKGROUND OF THE INVENTION

There is an increasing consumer demand for meat products having low fat content. This demand is fueled by accumulating evidence in the scientific literature that a high consumption of animal fat, especially fat with a high proportion of saturated fatty acids, represents a significant health hazard, including risk for cardiovascular disease. Other health concerns associated with high fat meats include their high content of cholesterol and the addition of relatively high amounts of salt which are added to improve the binding characteristics since salt aids in extracting the native water binding component myosin from the meat. Furthermore, an increasing number of consumers find meat products containing chemical additives such as phosphates, emulsifying additives, and anti-oxidants less acceptable.

Faced with consumers who seek a healthier meat product, meat producers are continually pressed to offer cheaper and healthier products.

Cheaper products, of course, come from lowering costs of production. Producers are always interested in improving the growth rate and feed conversion of their animals. Lower production costs come from the shorter time to market and lower costs of feeding an animal. This can increase the profit margin in the livestock industry and/or result in lower prices to the consumer.

By being able to select for animals which have the aforementioned traits, producers can raise animals with these desirable characteristics. Selection for desirable traits has traditionally been done using breeding techniques.

Genetic differences exist among individual meat producing animals as well as among breeds which can be exploited by breeding techniques to achieve animals with these desirable characteristics. For example, Chinese breeds are known for reaching puberty at an early age and for their large litter size, while American breeds are known for their greater growth rates and leanness. Thus, it would be desirable to combine the best characteristics of both types of these breeds, thereby improving pork production.

Often, however, heritability for desired traits is low, for example, heritability for litter size is around 10%–15%. Standard breeding methods which select individuals based upon phenotypic variations do not take fully into account genetic variability or complex gene interactions which exist. Therefore, there is a need for an approach that deals with selection for leanness, growth rate, and feed consumption at the cellular or DNA level. This method will provide a method for genetically evaluating animals to enable breeders to more accurately select those animals which not only phenotypically express desirable traits but those which express favorable underlying genetic criteria. This has largely been accomplished to date by marker assisted selection.

Restriction fragment length polymorphism (RFLP) analysis has been used by several groups to study pig DNA. Jung et al., *Theor. Appl. Genet.*, 77:271–274 (1989), incorporated herein by reference, discloses the use of RFLP techniques to show genetic variability between two pig breeds. Polymorphism was demonstrated for swine leukocyte antigen (SLA) Class I genes in these breeds. Hoganson et al., *Abstract for Annual Meeting of Midwestern Section of the American Society of Animal Science*, Mar. 26–28, 1990, incorporated herein by reference, reports on the polymorphism of swine major histocompatibility complex (MHC) genes for Chinese pigs, also demonstrated by RFLP analysis. Jung et al., *Animal Genetics*, 26:79–91 (1989), incorporated herein by reference, reports on RFLP analysis of SLA Class I genes in certain boars. The authors state that the results suggest that there may be an association between swine SLA/MIHC Class I genes and production and performance traits. They further state that the use of SLA Class I restriction fragments, as genetic markers, may have potential in the future for improving pig growth performance.

The ability to follow a specific favorable genetic allele involves a novel and lengthy process of the identification of a DNA molecular marker for a major effect gene. The marker may be linked to a single gene with a major effect or linked to a number of genes with additive effects. DNA markers have several advantages; segregation is easy to measure and is unambiguous, and DNA markers are co-dominant, i.e., heterozygous and homozygous animals can be distinctively identified. Once a marker system is established selection decisions could be made very easily, since DNA markers can be assayed any time after a tissue or blood sample can be collected from the individual infant animal.

The use of genetic differences in receptor genes has become a valuable marker system for selection. For example, U.S. Pat. Nos. 5,550,024 and 5,374,526 issued to Rothschild et al. disclose a polymorphism in the pig estrogen receptor gene which is associated with larger litter size, the disclosure of which is incorporated herein by reference. U.S. application Ser. No. 08/812,208 discloses polymorphic markers in the pig prolactin receptor gene which are associated with larger litter size and overall reproductive efficiency.

It can be seen from the foregoing that a need exists for a method for selecting animals with the improved metabolic traits regarding fat content, growth rate, and feed consumption.

SUMMARY OF THE INVENTION

An object of the present invention is to provide a genetic marker based on or within the MC4R gene which is indicative of fat content, growth rate, and/or feed consumption.

Another object of the invention is to provide an assay for determining the presence of this genetic marker.

A further object of the invention is to provide a method of evaluating animals that increases accuracy of selection and breeding methods for the desired traits.

Yet another object of the invention is to provide a PCR amplification test which will greatly expedite the determination of presence of the marker.

An additional object of the invention is to provide a kit for evaluating a sample of animal DNA for the identified genetic marker.

These and other objects, features, and advantages will become apparent after review of the following description and claims of the invention which follow.

This invention relates to the discovery of a polymorphism within the melanocortin-4 receptor (MC4R) gene which is associated with fat content, growth rate, and feed conversion traits in animals. According to the invention, the association of the MC4R polymorphism with the trait(s) enables genetic markers to be identified for specific breeds or genetic lines. The TaqI restriction pattern which identifies the polymorphism is used to assay for the presence or absence of markers associated with the desirable metabolic traits. The breed-dependent marker genotype (i.e., a marker in some breeds and a nonmarker in others) consists of a polymorphism within MC4R, a guanine to adenine transition at position 678 of the PCR product (a missense mutation of aspartic acid codon (GAU) into asparagine codon (AAU) at position 298 amino acid of the MC4R protein). The invention includes assays for detection of the marker as well as the sequence characterization of the polymorphism and includes novel sequences in the MC4R gene which may be used to design amplification primers for such an assay. Additionally, the invention includes a method for using the assay in breeding programs for animal selection and a kit for performing the assay.

Definitions

As used herein, "low fat content" or "leanness" means a biologically significant decrease in body fat relative to the mean of a given population.

BRIEF DESCRIPTION OF THE DRAWINGS

FIGS. 1 and 1A are the sequence listing for MC4R in pigs (SEQ ID NO:1). "X" represents the site of the polymorphism.

FIGS. 2A, 2B and 2C represent a comparison of the DNA sequence between the human (SEQ ID NO:2) and the porcine (SEQ ID NO:3) MC4R gene.

FIGS. 3A and 3B represent a comparison of the amino acid sequence between the human (SEQ ID NO:4) and the porcine (SEQ ID NO:5) MC4R gene.

FIGS. 4a, 4b, 4c and 4d are linkage reports for MC4R from CRI-MAP.

FIG. 5 depicts partial nucleotide and amino acid sequences (SEQ ID NO:11) of the porcine MC4R gene. The amino acid translation shows an amino acid substitution at codon 298.

FIG. 7 depicts multiple-alignments of the putative seventh transmembrane domain of porcine MC4R with other MCRs and GPCRs. The "*" represents the predicted sequence positions for porcine MC4R. The other amino acid sequences were obtained from the GenBank database (accession numbers P32245 (SEQ ID NO:12), P70596 (SEQ ID NO:13), P41983 (SEQ ID NO:14), P56451 (SEQ ID NO:15), P34974 (SEQ ID NO:16), P41968 (SEQ ID NO:17), P33033 (SEQ ID NO:18), Q01718 (SEQ ID NO:19), Q01726 (SEQ ID NO:20), Q28031 (SEQ ID NO:21), AF011466 (SEQ ID NO:22), P21554 (SEQ ID NO:23), P18089 (SEQ ID NO:24), P30680 (SEQ ID NO:25), P47211 (SEQ ID NO:26). The missense variant in porcine MC4R substituted amino acid N for D in the position marked with an arrow. The Asp (D) residue is highly conserved among MCRs, and the Asn (N) residue is well conserved in most other GPCRs.

DETAILED DESCRIPTION OF THE PREFERRED EMBODIMENT

Figure 6:
FIG. 6 is an electrophoresis gel of TaqI digestion of the PCR product. Molecular marker (M) and MC4R genotypes are indicated at the top of each lane.

Obesity is a disease affecting energy balance. The control of energy metabolism is simple: store excessive energy as fat and manage the energy to avoid superfluous energy storage, i.e., obesity. Although several genes and signaling systems have been implicated in obesity, there has been little known about the interconnection of energy homeostatic mechanism and genetic polymorphism. The melanocortin-4 receptor (MC4R) has been shown to be an important mediator of long term weight homeostasis. MC4R antagonists can increase food intake and body weight during chronic administration. Skuladottir, G. V., et al., "Long term orexigenic effect of a novel melanocortin 4 receptor selective antagonist", *British J. of Pharm.*, 126(1):27–34 (1999).

Lu et al. (1994) suggested that the melanocortin receptors are involved in controlling food intake and energy balance through studying its antagonism to the agouti obesity syndrome. Huszar et al. (1997) found that inactivation of the melanocortin-4 receptor gene (MC4R) resulted in a maturity onset obesity syndrome in mice and demonstrated a major role of MC4R protein in the regulation of energy balance related to the agouti obesity syndrome. In addition, the MC4R protein mediates the effects of leptin, one of the important signaling molecules in energy homeostasis (Seeley et al. 1997).

According to the present invention, a variant or polymorphism in the MC4R gene has been located, and this genetic variability is associated with phenotypic differences in the metabolic traits of fat content, growth rate, and/or feed consumption.

In one embodiment of the invention, an assay is provided for detection of presence of a desirable genotype. The assay involves amplifying the genomic DNA purified from blood, tissue, semen, or other convenient source of genetic material by the use of primers and standard techniques, such as the polymerase chain reaction (PCR), then digesting the DNA with a restriction enzyme (e.g., Taq I) so as to yield gene fragments of varying lengths, and separating at least some of the fragments from others (e.g., using electrophoresis).

The fragments may also be detected by hybridizing with a nucleotide probe (e.g., radio-labeled cDNA probes) that contains all or at least a portion of the MC4R gene cDNA sequence to the separated fragments and comparing the results of the hybridization with assay results for a gene sequence known to have the marker or a sequence known to not have the marker. Selection and use of probes for detection of MC4R sequences based on the known and disclosed MC4R sequences is generally known to those skilled in the art. The probe may be any sequence which will hybridize to the separated digestion products and allow for detection.

Another embodiment of the invention provides a kit for assaying the presence in a MC4R gene sequence of a genetic marker. The marker being indicative of inheritable traits of fat content, growth rate, and/or feed consumption. The kit in a preferred embodiment also includes novel PCR primers comprising 4–30 contiguous bases on either side of the polymorphism to provide an amplification system allowing for detection of the Taq I polymorphism by PCR and Taq I digestion of PCR products. The preferred primers are SEQ ID NO: 7 and SEQ ID NO: 8.

A further embodiment comprises a breeding method whereby an assay of the above type is conducted on a plurality of gene sequences from different animals or animal embryos to be selected from and based on the results, certain animals are either selected or dropped out of the breeding program.

According to the invention, the polymorphism in the MC4R gene, identifiable by the Taq I restriction pattern, is disclosed. As is known in the art, restriction patterns are not exact determinants of the size of fragments and are only approximate. The polymorphism is identifiable by three bands from a Taq I digestion of the PCR product, 466, 225, and 76 base pairs (bp) for one homozygous genotype (allele 1); two bands, 542 and 225 bp for another homozygous genotype (allele 2); and four bands for the heterozygous genotype (542, 466, 225, and 76 bp). The marker for leanness and lower feed intake is identifiable by the 466/225/76 bands, except for the Chinese pigs, where the Chinese pigs' marker for leanness is the 542/225 bands. The marker for faster rate of gain is identifiable by the 542/225 bands.

In addition, the polymorphism associated with the pattern has been identified at the nucleotide level. The polymorphic Taq I site was sequenced along with the general surrounding area. See SEQ ID NO: 1. The sequences surrounding the polymorphism have facilitated the development of a PCR test in which a primer of about 4–30 contiguous bases taken from the sequence immediately adjacent to the polymorphism is used in connection with a polymerase chain reaction to greatly amplify the region before treatment with the Taq I restriction enzyme. The primers need not be the exact complement; substantially equivalent sequences are acceptable.

From sequence data, it was observed that in allele 2 the guanine is substituted with an adenine at position 678 of the PCR product or at position 298 amino acid of the MC4R protein changing the aspartic acid codon (GAU) into an asparagine codon (AAU). The PCR test for the polymorphism used a forward primer of 5'-TGG CAA TAG CCA AGA ACA AG-3' (SEQ. ID NO: 5) and a reverse primer of 5'-CAG GGG ATA GCA ACA GAT GA-3' (SEQ. D NO: 6). Pig specific primers used were a forward primer of 5'-TTA AGT GGA GGA AGA AGG-3' (SEQ. ID NO: 7) and a reverse primer of 5'-CAT TAT GAC AGT TAA GCG G-3' (SEQ ID NO: 8). The resulting amplified product of about 750 bp, when digested with Taq I, results in allelic fragments of 466, 225, and 76 bp (allele 1) or 542 and 225 bp (allele 2).

The marker may be identified by any method known to one of ordinary skill in the art which identifies the presence or absence of the marker, including for example, single-strand conformation polymorphism analysis (SSCP), RFLP analysis, heteroduplex analysis, denaturing gradient gel electrophoresis, and temperature gradient electrophoresis, ligase chain reaction or even direct sequencing of the MC4R gene and examination for the Taq I RFLP recognition pattern.

One or more additional restriction enzymes and/or probes and/or primers can be used. Additional enzymes, constructed probes, and primers can be determined by routine experimentation by those of ordinary skill in the art.

Other possible techniques include non-gel systems such as TAQMAN™ (Perkin Elmer). In this system, oligonucleotide PCR primers are designed that flank the mutation in question and allow PCR amplification of the region. A third oligonucleotide probe is then designed to hybridize to the region containing the base subject to change between different alleles of the gene. This probe is labeled with fluorescent dyes at both the 5' and 3' ends. These dyes are chosen such that while in this proximity to each other the fluorescence of one of them is quenched by the other and cannot be detected. Extension by Taq DNA polymerase from the PCR primer positioned 5' on the template relative to the probe leads to the cleavage of the dye attached to the 5' end of the annealed probe through the 5' nuclease activity of the Taq DNA polymerase. This removes the quenching effect allowing detection of the fluorescence from the dye at the 3' end of the probe. The discrimination between different DNA sequences arises through the fact that if the hybridization of the probe to the template molecule is not complete, i.e., there is a mismatch of some form, the cleavage of the dye does not take place. Thus, only if the nucleotide sequence of the oligonucleotide probe is completely complementary to the template molecule to which it is bound will quenching be removed. A reaction mix can contain two different probe sequences each designed against different alleles that might be present, thus, allowing the detection of both alleles in on reaction.

Though the use of RFLPs is one method of detecting the polymorphism, other methods known to one of ordinary skill in the art may be used. Such methods include ones that analyze the polymorphic gene product and detect polymorphisms by detecting the resulting differences in the gene product.

Though the preferred method of separating restriction fragments is gel electrophoresis, other alternative methods known to one skilled in the art may be used to separate and determine the size of the restriction fragments.

It is possible to indirectly select for the polymorphism with alternative DNA markers. It is possible to establish a linkage between specific alleles of alternative DNA markers and alleles of DNA markers known to be associated with the MC4R gene which have previously been shown to be associated with a particular trait. Examples of markers on the published PiGMaP chromosome map which are linked to the MC4R gene include S0331, BHT0433, and S0313.

The reagents suitable for applying the methods of the present invention may be packaged into convenient kits. The kits provide the necessary materials, packaged into suitable containers. At a minimum, the kit contains a reagent that identifies the polymorphism in the MC4R gene that is associated with the traits of interest, fat content, growth rate, and feed consumption. Preferably, the reagent that identifies the polymorphism is a PCR set (a set of primers, DNA polymerase, and four nucleoside triphosphates) that hybridize with the MC4R gene or a fragment thereof. Preferably, the PCR set and restriction enzyme that cleaves the MC4R gene in at least one place are included in the kit. Preferably, the kit further comprises additional means, such as reagents, for detecting or measuring the detectable entity or providing a control. Other reagents used for hybridization, prehybridization, DNA extraction, visualization, and similar purposes may also be included, if desired.

The genetic markers, methods, and kits of the invention are useful in a breeding program to improve fat content, growth rate, and feed consumption characteristics in a breed, line, or population of animals. Continuous selection and breeding of animals that are at least heterozygous and preferably homozygous for the desired polymorphism associated with the particular trait would lead to a breed, line, or population having those desired traits. Thus, the marker is a selection tool.

The following examples are offered to illustrate, but not limit the invention.

EXAMPLE 1

Melanocortin 4 Receptor PCR-RFLP Test—TaqI Polymorphism and Genetic Linkage Mapping of MC4R Gene Primers:

Primers were designed from homologous regions of human and rat MC4R sequences (Genbank Accession No. s77415 and u67863, respectively). These primers were used to amplify a 750-bp sequence of the porcine MC4R gene.

MC4R1: 5'-TGG CAA TAG CCA AGA ACA AG 3' (SEQ ID NO: 5)

MC4R4: 5'-CAG GGG ATA GCA ACA GAT GA 3' (SEQ ID NO: 6)

PCR Conditions:

| Mix 1: | 10X Promega Buffer | 1.0 µL |
|---|---|---|
| | 25 mM MgCl₂ | 0.6 µL |
| | dNTPs mix (2.5 mM each) | 0.5 µL |
| | 25 pmol/µL MC4R1 | 0.1 µL |
| | 25 pmol/µL MC4R4 | 0.1 µL |
| | dd sterile H₂O | 7.5 µL |
| | Taq Polymerase (5 U/µL) | 0.07 µL |
| | Genomic DNA (12.5 ng/µL) | 1.0 µL |

Ten µL of Mix 1 and DNA were combined in reaction tube, then overlaid with mineral oil. The following PCR program was run: 94° C. for 2 min.; 35 cycles of 94° C. for 30 sec.; 58° C. 1 min., and 72° C. 1 min. 30 sec.; followed by a final extension at 72° C. for 15 min.

Five µl of the PCR reaction product was checked on a standard 1% agarose gel to confirm amplification success and clean negative control. Product size is approximately 750 base pairs. Digestion was performed by the following procedure.

| TaqI Digestion Reaction | 10 µL reaction |
|---|---|
| PCR product | 5.0 µL |
| 10X TaqI NE Buffer | 1.0 µL |
| BSA (10 mg/ml) | 0.1 µL |
| TaqI enzyme (20 U/µL) | 0.5 µL |
| dd sterile H₂O | 3.4 µL |

A cocktail of the buffer, enzyme, BSA, and water was made. Five µL was added to each reaction tube containing the DNA. The mixture was then incubated at 65° C. for at least 4 hours to overnight. Loading dye was mixed with the digestion reaction and the total volume was loaded on a 3% agarose gel. The major bands for allele 1 are about 466, 225, and 76 bp. The allele 2 genotype bands are 542 and 225 bp. The heterozygote genotype has both allele 1 and allele 2.

Results

The amplified PCR product is about 750 bp. The sequence of the PCR product confirmed that the PCR product is MC4R gene with 97.6%, and 92.2% identities at the amino acid and DNA level, respectively, to corresponding human sequences. (see FIGS. 2 and 3).

The TaqI digestion of the PCR product produced allelic fragments of 466, 225, and 76 bp (allele 1), or 542 and 225 bp (allele 2). The heterozygote genotype has both types of alleles. Mendelian inheritance was observed in three three-generation international reference families, which were used to map this gene by linkage analysis.

The polymorphism between allele 1 and allele 2 resulting from a G e A transition at position 678 of the PCR product revealed a missense mutation of Aspartic acid codon (GAU) into Asparagine codon (AAU) at position 298 amino acid of MC4R protein. (See FIG. 1, SEQ ID NO:1).

Allele frequencies were determined by genotyping of DNA samples from a small number of animals from different breeds (Table 1). Allele 1 was observed with a frequency of 1 in Meishan, but was not observed or observed at very low frequency in Hampshire and Yorkshire. The frequencies of allele 1 in Landrace and Chester White were 0.5, respectively.

FIGS. 2 and 3 illustrate the differences between the DNA and amino acid sequences of the human and porcine MC4R gene (SEQ ID NOS: 1–4).

TABLE 1

The Frequency of Allele 1 in Different Pig Breeds

| Breed | # Animals | Freq. Allele 1 |
|---|---|---|
| Meishan | 8 | 1 |
| Large White | 8 | 0.56 |
| Yorkshire | 6 | 0.08 |
| Hampshire | 5 | 0 |
| Landrace | 4 | 0.5 |
| Chester White | 4 | 0.5 |
| Minzu | 2 | 1 |
| Wild Boar | 2 | 1 |

Linkage Analyses

Two-point and multi-point linkage analyses were performed on the genotypes of international reference families. See FIGS. 4a–4c. The data were analyzed by using the CRI-MAP program. MC4R was significantly linked to several markers on porcine chromosome (SSC) 1. The most closely linked markers (recombination fraction and LOD score in parentheses) are SO331 (0.02, 21.97), BHT0433 (0.02, 21.32), and SO313 (0.00, 17.76) by two-point linkage analysis. A multi-point linkage analysis produced the best map order of markers and MC4R (with distance in Kosambi cM): KGF-5.8-CAPN3-2.5-MEF2A-6.1-MC4R-5.6-SO313.

Somatic cell hybrid panel of pig and rodent was used to assign MC4R to a cytogenetic region. PCR products from pig specific primers were amplified in clones 7, 8, 16, 18, and 19. MC4R was localized to SSC1q 22–27.

EXAMPLE 2

MC4R Receptor PCR-RFLP Test Using Pig Specific Primers and Genetic Linkage Mapping of the Porcine MC4R Gene Pip Specific Primer Sequences Forward primer 5'-TTA AGT GGA GGA AGA AGG-3' (SEQ ID NO: 7)

Reverse primer: 5'-CAT TAT GAC AGT TAA GCG G-3' (SEQ ID NO: 8)

Method of Detection

The PCR reaction was performed using

| | |
|---|---|
| Porcine genomic DNA | 12.5 ng |
| 1x PCR buffer | |
| MgCl$_2$ | 1.5 mM |
| dNTP | 0.125 mM |
| Forward primer | 0.3 µM |
| Reverse primer | 0.3 µM |
| Taq DNA polymerase (Promega) | 0.35 U | in a 10 µL final volume. The PCR profile included 2 min. at 94° C.; 35 cycles of 30 sec. at 94° C., 1 min. at 56° C., 1 min. 30 sec. at 72° C.; and 15 min. at 72° C. in a Robocycler (Statagene, La Jolla, Calif.). A 5.0 µL aliquot of the PCR products was digested in a total volume of 10 µL with 10 U of TaqI incubated overnight at 65° C. The digestion products were electrophoresed on a 3% agarose gel.

Description of Polymorphism

The TaqI digestion of the PCR product produced fragments of 466, 225, and 76 bp in allele 1 and 542 and 225 bp in allele 2. The heterozygous genotype has fragments of both allele 1 and allele 2.

Pattern of Inheritance

Autosomal segregation of Mendelian inheritance was observed in three three-generation European PiGMaP families (Archibald et al., 1995).

Allele Frequencies

Allele frequencies were determined by genotyping the grandparental animals of the European PiGMaP families and unrelated animals from ISU reference families. Allele 1 was observed with the following frequencies.

TABLE 2

The Frequency of Allele 1 in Different Pig Breeds

| Breed | # Animals | Freq. Allele 1 |
|---|---|---|
| Meishan | 8 | 1 |
| Large White | 8 | 0.56 |
| Yorkshire | 10 | 0.15 |
| Hampshire | 12 | 0 |
| Landrace | 8 | 0.56 |
| Chester White | 8 | 0.56 |
| Minzu | 2 | 1 |
| Wild Boar | 2 | 1 |

Chromosomal Location

Two-point and multi-point linkage analysis were performed on the genotypes of three PiGMaP families using the CRI-MAP program (Green et al. 1990). MC4R was significantly linked to several markers on porcine chromosome 1 (SSC 1). The most closely linked markers (recombination fraction and LOD score in parentheses) are SO331 (0.02, 21.97), BHT0433 (0.02, 21.32), and SO313 (0.00, 17.76) according to two-point linkage analysis. The best map order of MC4R with respect to other linked markers produced by multi-point linkage analysis is as follows (with distance in Kosamnbi cM): KGF-5.8-CAPN3-2.5-MEF2A-6.1-MC4R-5.6-SO313.

Comments

The Melanocortin-4 Receptor is a G protein-coupled, seven-transmembrane receptor expressed in the brain. Huszar et al. (1997) found that inactivation of MC4R gene resulted in a maturity onset obesity syndrome in mice and demonstrated a major role of MC4R protein in the regulation of energy balance. The MC4R gene has been mapped to human chromosome 18q21.3 (Gantz et al., 1993). The localization of MC4R gene to SSC 1 is consistent with previous chromosome painting data indicating synteny between this chromosome and HSA 18 and 15 (Goureau et al., 1996). However, the gene order of several genes previously mapped from HSA 18 and 15 to SSC 1, including CAPN3, KGF, and MEF2A, is not conserved with MC4R. Therefore, mapping of MC4R to SSC 1 may identify an evolutionary breakpoint between HSA 18 and 15 in relation to SSC 1.

EXAMPLE 3

Association of Marker with Enhanced Metabolic Characteristics

In a preliminary study to determine which allele is associated with which trait and in which breeds, the genotypes of several lines of animals were correlated with days to 110 kg, backfat measurements, daily gains, and average daily feed intake. The pigs used in the study were from lines from Pig Improvement Company (PIC).

Data was accumulated using the PCR test described supra for the 1 and 2 allele of the MC4R gene. The collected data is summarized in Tables 3–8 below.

According to the results, allele 1 is the significantly leaner allele (see P2 backfat measurements) in all lines except in Chinese pigs where it is the fat allele. Allele 2 is associated with significantly faster rate of gain (test daily gain) in the tested commercial lines. Overall allele 1 is associated with lower feed intake.

TABLE 3

| MC4R genotype | Number of observations | | | | | |
|---|---|---|---|---|---|---|
| | L02 | L03 | L19 | L65 | Overall | L95 |
| 11 | 88 | 30 | | 32 | 150 | 20 |
| 12 | 57 | 54 | 56 | 74 | 241 | 67 |
| 22 | 12 | 31 | 254 | 33 | 330 | 37 |
| | | | | Total | 721 | |

MC4R genotype:
11 = homozygous allele 1
12 = heterozygous
22 = homozygous allele 2

TABLE 4

| MC4R genotype | Number of observations (males/females) | | | | | |
|---|---|---|---|---|---|---|
| | L02 | L03 | L19 | L65 | Overall | L95 |
| 11 | 9/79 | 12/18 | | 15/17 | 36/114 | 0/20 |
| 12 | 9/48 | 37/17 | 12/44 | 44/30 | 102/139 | 0/67 |
| 22 | 3/9 | 28/3 | 89/165 | 21/12 | 141/189 | 0/37 |

TABLE 5

Days to 110 kg

| MC4R genotype | L02 | L03 | L19 | L65 | Overall | L95 |
|---|---|---|---|---|---|---|
| 11 | 169.7 | 172.4 |  | 169.6 | 168.5 | 219.1 |
| 12 | 170.2 | 171.5 | 165.0 | 171.2 | 168.7 | 212.2 |
| 22 | 165.3 | 173.4 | 162.9 | 170.3 | 167.1 | 211.4 |
|  | P < .23 | P < .75 | P < .15 | P < .76 | P < .31 | P < .27 |

TABLE 6

P2 backfat (mm)

| MC4R Genotype | L02 | L03 | L19 | L65 | Overall | L95 |
|---|---|---|---|---|---|---|
| 11 | 10.8 | 11.9 |  | 9.7 | 11.1 | 22.8 |
| 12 | 11.3 | 12.5 | 12.2 | 10.5 | 11.8 | 21.5 |
| 22 | 12.1 | 12.7 | 12.6 | 10.7 | 12.1 | 20.3 |
|  | P < .10 | P < .43 | P < .34 | P < .17 | P < .006 | P < .17 |

TABLE 7

Test daily gain (gm/d)

| MC4R genotype | L02 | L03 | L19 | L65 | Overall | L95 |
|---|---|---|---|---|---|---|
| 11 | 882.2 | 811.0 |  | 881.8 | 871.9 | 688.8 |
| 12 | 891.2 | 820.5 | 875.6 | 873.0 | 876.3 | 676.2 |
| 22 | 969.1 | 819.5 | 906.7 | 906.2 | 906.9 | 692.5 |
|  | P < .01 | P < .96 | P < .05 | P < .24 | P < .006 | P < .66 |

TABLE 8

Average daily feed intake (kg/d), boars only, except L95 which was gilts only

| MC4R genotype | L02 | L03 | L19 | L65 | Overall | L95 |
|---|---|---|---|---|---|---|
| 11 | 2.31 | 1.78 |  | 1.75 | 1.89 | 2.05 |
| 12 | 2.11 | 1.90 | 1.97 | 1.90 | 1.96 | 2.03 |
| 22 | 2.15 | 1.97 | 2.00 | 1.97 | 2.02 | 2.08 |
|  | P < .84 | P < .14 | P < .56 | P < .14 | P < .16 | P < .36 |

EXAMPLE 4

A Missense Variant of the Porcine Melanocortin-4 Receptor (MC4R) Gene is Associated with Fatness, Growth, and Feed Intake Traits To determine if there was an association of this MC4R polymorphism with phenotypic variation the mutation was tested in a large number of individual animals from several different pig lines. Analyses of growth and performance test records showed significant associations of MC4R genotypes with backfat, growth rate and feed intake in a number of lines. It is probable that the variant amino acid residue of the MC4R mutation causes a significant change of the MC4R function. These results support the functional significance of a pig MC4R missense mutation and suggest that comparative genornics based on model species may be equally important for application to farm animals as they are for human medicine.

Identification of mutations in the leptin and the leptin receptor has provided some information on genetic components involved in the regulation of energy balance (Zhang et al. 1994; Tartaglia et al. 1995). Genetic studies using animal models have facilitated the identification of major genetic causes of obesity (Andersson 1996; Pomp 1997; Giridharan 1998). Furthermore, several other genes involved in the neural signaling pathway of energy homeostasis have been identified (Flier and Maratos-Flier 1998; Schwartz et al. 1999). Of particular interest among candidate signaling molecules involved in the regulation of energy homeostasis is the melanocortin-4 receptor (MC4R). The MC4R response to leptin signaling is a link between food intake and body weight (Seeley et al. 1997; Marsh et al. 1999). Neuropeptide Y (NPY) signaling in the central nervous system is also mediated by the MC4R protein (Kask et al. 1998). Several mutations in MC4R including frameshift and nonsense mutations are associated with dominantly inherited obesity in humans (Vaisse et al. 1998; Yeo et al. 1998). Some other MC4R missense mutations in humans have also been identified (Gotoda et al. 1997; Hinney et al. 1999) but the functional significance of these mutations has not been characterized.

Selection based on growth characteristics has been of great importance to the pig industry because of costs associated with feeding and consumer preference for lean meat. Efficient genetic improvement in these quantitative traits may be augmented through the use of marker assisted selection (MAS) using high density genetic maps (Dekkers and van Arendonk 1998; Rothschild and Plastow 1999). An important tool in this process is comparative mapping using the well-developed human and mouse gene maps, which assist in the identification of corresponding genomic regions or major genes controlling growth and performance traits in the pig. Biological understanding of complex traits in human or model species offers an alternative approach to identify genes responsible for the traits of economic interest in livestock. Several quantitative trait loci (QTL) linkage scans using phenotypically divergent breeds and candidate gene analyses have been successfully conducted for fatness and growth traits (Yu et al. 1995; Casas-Carrillo et al. 1997; Knorr et al. 1997; Knott et al. 1998; Rohrer et al. 1998; Wang et al. 1998; Paszek et al. 1999), but no individual genes with major effects on growth and performance traits have yet been established for commercial populations. The role of MC4R in feed intake and obesity suggests it may be an important genetic marker for the growth-related traits in the pig.

Materials and Methods

Animals. Pigs were raised under normal production conditions under the care of PIC employees in nucleus farms in the United States and Europe. Pigs were put on the performance test at approximately 70 days of age and taken off test after 13 weeks. At the end of the trial backfat was measured ultrasonically in real time (B mode) at the $10^{th}$ rib 2 cm from the centerline. Average daily gain (growth) over the test period was calculated as weight gained divided by days on test. Days to 110 kg market weight was estimated using standard procedures and feed intake was measured using individual electronic measurement equipment.

PCR amplification of a pig MC4R gene fragment. Primers were designed from homologous regions of human and rat MC4R sequences (GenBank accession no. s77415 and u67863, respectively). The primers were: forward primer: 5'-TGG CAA TAG CCA AGA ACA AG-3' (SEQ. ID NO:5) and reverse primer: 5'-CAG GGG ATA GCA ACA GAT GA-3' (SEQ. ID NO:6). The PCR reaction was performed using 12.5 ng of porcine genomic DNA, 1× PCR buffer, 1.5 mM MgCl$_2$, 0.125 mM dNTPs, 0.3 mM of each primer, and 0.35 U Taq DNA polymerase (Promega) in a 10 µL final volume. The conditions for PCR were as follows: 2 min at 94° C.; 35 cycles of 30 s at 94° C., 1 min at 56° C., 1 min 30 s at 92°C., and a final 15 min extension at 72° C. in a Robocycler (Stratagene, La Jolla, Calif.).

Sequencing and mutation detection. Sequencing of the PCR products from several individual pigs of different breeds was conducted and the sequences were compared to detect any nucleotide change. Sequencing was performed on an ABI sequencer 377 (Applied Biosystems). The porcine MC4R sequence has been submitted to GenBank, and has accession number AF087937. The sequence analysis revealed one nucleotide substitution situated within a TaqI restriction enzyme recognition site (Kim et al. 1999). A set of primers was then designed to generate a smaller MC4R gene fragment, which contained only one informative TaqI restriction site to specify the polymorphic site and to facilitate the PCR-RFLP test. These primers were: forward 5'-TAC CCT GAC CAT CTT GAT TG-3' (SEQ. ID NO:10) and reverse: 5'-ATA GCA ACA GAT GAT CTC TTT G-3' (SEQ. ID NO:11).

Statistical analysis. Analysis of variance procedures were used with a mixed model that accounted for the fixed effects of farm, test period, sex of the animal, the MC4R genotype and site (random). All animals in lines of American/European descent (Lines A–D) were pooled for the overall analysis and in this analysis line of origin was included. Mean effects were estimated for each genotype and are presented in Tables 9–15. Overall F tests were used to determine level of significance.

Results

Identification of a missense mutation in the pig MC4R gene. The MC4R gene consists of approximately 1 kb of coding sequence contained within a single exon. About 750 bp of a pig MC4R gene fragment was produced by PCR (Kim et al. 1999). The sequence of the PCR product confirmed that the PCR product is the MC4R gene with 92.2% and 97.6% identities at nucleotide and the amino acid levels, respectively, to the human MC4R sequence. Multiple alignments of the sequences from individual animals of several breeds identified a single nucleotide substitution (G→A; FIG. 5). The polymorphism revealed a missense mutation that replaces aspartic acid (GAU) with asparagine (AAU) at the position identical to amino acid 298 of human MC4R protein. To confirm this base change, we designed pig-specific primers flanking the polymorphic site and analyzed the polymorphism as a TaqI PCR-RFLP gel (FIG. 6). FIG. 6 shows a TaqI digestion of the PCR product analyzed by agarose-gel electrophoresis. Allele 1 produced 156 and 70 bp fragments and allele 2 produced a 226 bp fragment as the PCR-RFLP. The heterozygote has both allele 1 and 2 fragments. Molecular marker (M) and MC4R genotypes are indicated at the top of each lane.

The MC4R missense mutation is within a highly conserved region among melanocortin receptors (MCR). The MCR is a subfamily of G-protein coupled receptors (GPCR) containing certain conserved structural elements common to most other GPCRs, but overall amino acid identities between MCR and other GPCRs are low (Tatro 1996). A multiple-alignment of the predicted amino acid sequences of the pig MC4R with MC4R proteins from other species, other MCR proteins, or representative GPCRs showed that the aspartic acid found at position 298 of the seventh transmembrane domain is very highly conserved in the MCR proteins (FIG. 7). It is interesting to note, however, that this position is occupied by asparagine in most other GPCRs. The MCR proteins show 40–80% amino acid identity with each other (Tatro 1996), but the second intracytoplasmic loop and the seventh transmembrane domain are highly conserved among MCR proteins (Gantz et al. 1993). Some of the relationships between MCR structure and function have been discovered by the studies of natural and experimental mutations in humans and mice (Robbins et al. 1993; Valverde et al. 1995; Frandberg et al. 1998). These studies indicate that some mutations in highly conserved regions cause structural changes and alter the function of the receptor. The Asp298Asn substitution mutation could have an effect on the function of the receptor. However, this will require further testing but it is known that change of the homologous residue in MC1R (Asp294His) is associated with fair skin and red hair in humans (Valverde et al. 1995).

The MC4R missense mutation is associated with obesity-related traits. To investigate the effects of the missense mutation, the relationship of MC4R genotypes was analyzed for the effects on variation in growth rate, backfat, and feed consumed in over 1,800 animals from several commercial pig lines from PIC, an international pig breeding company. The animals were from closed commercial lines of European/American breeds (Lines A–D) together with a line originating from a cross between a European and a Chinese breed (Line E). In lines A–D significant associations of the MC4R genotypes were found for all performance traits. The animals homozygous for allele 1 had on average significantly less backfat (P<0.001), lower daily gain (P<0.001), and lower feed intake(P<0.01) than those of the homozygous 22 genotype animals (Tables 11, 13, & 15). Overall, pigs with the 11 genotype had approximately 9% less backfat than pigs with the 22 genotype (Table 11), whereas pigs with the 22 genotype grow significantly faster (37g/day) than pigs with the 11 genotype (Table 13). These results appear to be a function of appetite because the 22 genotype animals consume considerably more feed (Table 15). The association between the missense variant of the MC4R gene and related performance traits is clearly established in European/American breeds. Although the number of tested animals is much smaller, these results were not seen in the considerably fatter Chinese crossed line (Line E). Interestingly, line E shows a trend for backfat in the opposite direction to that observed in the other lines (Table 11).

Discussion

The present study clearly demonstrates that the porcine MC4R missense mutation is significantly associated with several performance traits in pigs. Allele 1 representing Asp298, the well conserved amino acid within other MCR subtypes and other species MC4R, was associated with less backfat thickness, slower growth rate, and lower feed intake and allele 2 representing Asn298 was associated with fatter, higher feed intake, and faster growing animals. As the highly conserved residues in the melanocortin receptor proteins have important roles for ligand binding or intracellular signal transmission (Tatro 1996), the MC4R variants might exert functionally distinct abilities in the regulation of food intake and body weight. Further testing of this hypothesis will provide important insights into the structural basis of MCR function and a molecular target for the treatment of human obesity.

Allele 1 was associated with the fattest animals in Line E, which was derived by crossing a Chinese Large White breed with a line of Meishan origin. This is surprising given that the mutation causes a significant amino acid change in a well-conserved region. The result may be due to sampling. However, if we assume that this result will be significant when more results are added there are several possible explanations. One possibility could be the difference in the background gene effects (epistasis). As growth and fatness are complex polygenic traits, it is certainly possible that the Chinese breed has some distinct allelic interactions derived from several hundred years of isolation and these putative interaction(s) might create variation in polygenic traits within crosses between widely different lines (Frankel and Schork 1996). Several QTL analyses have been conducted for fatness and growth traits using divergent lines (Cases-Carrillo et al. 1997; Knott et al. 1998; Rohrer et al. 1998; Wang et al. 1998; Paszek et al. 1999), but QTL have not been reported near the C4R locus, which maps to chromosome 1 at approximately 80 cm on the linkage map (data not shown). It may mean that the epistatic effects of the MC4R alleles suggested in Line E have made it difficult to observe the MC4R locus in most QTL experiments which have involved crosses between Chinese and European/American lines. It is likely that the effect of some alleles will be variable in the different backgrounds and hard to detect in QTL experiments involving genetically divergent breeds.

The effect of MC4R variant will possibly be explained by further studies on the biological effect caused by this mutation in other pig breeds and lines. However, given the strong relationship of MC4R variants to leanness, growth and feed intake, this mutation could be used immediately for merker assisted selection (Meuwissen and Goddard 1996) to develop lines of pigs to satisfy particular customer requirements. For instance, in sow lines where appetite is normally decreased after farrowing, selection for the MC4R 2 allele could help improve feed intake. Furthermore, in some lines deemed to be too fat, selection for allele 1 could be employed and in lines that were considered too slow growth allele 2 selection could be also employed. Therefore, genotyping for the MC4R mutation in pig breeding lines will improve the selection efficiency of feed related production traits including growth and leanness. The candidate gene approach has also been used for investigating the role of the porcine leptin gene (Jiang and Gibson 1999). However, in the leptin case, although there was evidence for an association between a leptin polymorphism and backfat depth in a cross between a commercial breed and an unimproved line, there was no clear association in the different commercial lines tested (Jiang and Gibson 1999). Therefore, it should not be assumed that since one finds a gene that one can assume a relationship exists. In contrast, with MC4R we have determined that variation in this candidate gene can explain significant variation for backfat, growth rate, and feed intake in commercial lines of pigs. These results with MC4R illustrate the potential value of comparative genetic analyses using candidate genes in livestock genomics.

Effect of MC4R Genotype on Several Production Traits in the Pig

TABLE 9

| | Number of observations (males/females/totals) for Days to 110 kg and backfat | | | | | |
|---|---|---|---|---|---|---|
| MC4R | LINE A | LINE B | LINE C | LINE D | Total | Line E |
| 11 | 9/212/221 | 12/94/106 | | 37/17/54 | 58/323/381 | 0/20/20 |
| 12 | 9/150/159 | 37/96/133 | 12/158/170 | 152/30/182 | 210/434/644 | 0/67/67 |
| 22 | 3/16/19 | 28/36/64 | 89/356/445 | 155/12/167 | 275/420/695 | 0/37/37 |

TABLE 10

| | Days to 110 kg | | | | | |
|---|---|---|---|---|---|---|
| MC4R | LINE A | LINE B | LINE C | LINE D | Total | Line E |
| 11 | 166.3 +/− 0.8 | 168.4 +/− 1.4 | | 170.0 +/− 2.4 | 167.9 +/− 0.9 | 219.1 +/− 4.8 |
| 12 | 165.6 +/− 0.9 | 166.8 +/− 1.1 | 163.9 +/− 1.0 | 170.2 +/− 1.8 | 166.9 +/− 0.8 | 212.2 +/− 3.4 |
| 22 | 162.3 +/− 2.3 | 166.8 +/− 1.5 | 161.5 +/− 0.8 | 167.0 +/− 1.9 | 164.6 +/− 0.9 | 211.4 +/− 4.0 |
| | $P < .24$ | $P < .47$ | $P < .007$ | $P < .10$ | $P < .001$ | $P < .27$ |

TABLE 11

| | $10^{th}$ rib Backfat (mm) | | | | | |
|---|---|---|---|---|---|---|
| MC4R | LINE A | LINE B | LINE C | LINE D | Total | Line E |
| 11 | 10.7 +/− 0.2 | 12.1 +/− 0.2 | | 9.8 +/− 0.5 | 11.1 +/− 0.2 | 22.8 +/− 1.2 |
| 12 | 11.2 +/− 0.2 | 12.5 +/− 0.2 | 12.3 +/− 0.2 | 10.5 +/− 0.4 | 11.6 +/− 0.2 | 21.5 +/− 0.9 |
| 22 | 12.5 +/− 0.5 | 12.6 +/− 0.3 | 12.7 +/− 0.2 | 10.9 +/− 0.4 | 12.0 +/− 0.2 | 20.3 +/− 1.0 |
| | $P < .02$ | $P < .31$ | $P < .06$ | $P < .05$ | $P < .001$ | $P < .17$ |

TABLE 12

Number of observations (males/females/totals for Test daily gain

| MC4R | LINE A | LINE B | LINE C | LINE D | Total | Line E |
|---|---|---|---|---|---|---|
| 11 | 9/105/114 | 12/38/50 |  | 37/17/54 | 58/160/218 | 0/20/20 |
| 12 | 9/65/74 | 37/35/72 | 12/97/109 | 152/30/182 | 210/227/437 | 0/67/67 |
| 22 | 3/13/15 | 28/15/43 | 89/225/314 | 155/12/167 | 275/265/539 | 0/37/37 |

TABLE 13

Test daily gain (gm/day)

| MC4R | LINE A | LINE B | LINE C | LINE D | Total | Line E |
|---|---|---|---|---|---|---|
| 11 | 892.6 +/- 10.4 | 841.7 +/- 13.8 |  | 882.2 +/- 18.4 | 871.9 +/- 10.2 | 688.8 +/- 24.5 |
| 12 | 913.3 +/- 11.6 | 868.4 +/- 12.1 | 882.2 +/- 12.9 | 883.7 +/- 14.3 | 885.1 +/- 8.9 | 676.2 +/- 17.6 |
| 22 | 982.8 +/- 22.8 | 862.4 +/- 15.1 | 913.4 +/- 10.5 | 904.6 +/- 15.1 | 908.8 +/- 9.3 | 692.5 +/- 20.4 |
|  | P < .001 | P < .28 | P < .006 | P < .20 | P < .001 | P < .66 |

TABLE 14

Number of observations (males/females/total) for average daily feed intake

| MC4R | LINE A | LINE B | LINE C | LINE D | Total | Line E |
|---|---|---|---|---|---|---|
| 11 | 7/0/7 | 11/0/11 |  | 13/0/13 | 31.0/31 | 0/18/18 |
| 12 | 8/0/8 | 31/0/31 | 9/0/9 | 34/0/34 | 82/0/82 | 0/63/63 |
| 22 | 3/0/3 | 25/0/25 | 74/0/74 | 16/0/16 | 118/0/118 | 0/32/32 |

TABLE 15

Average daily feed intake (kg/day), boars only except LINE E which was gilts only

| MC4R | LINE A | LINE B | LINE C | LINE D | Total | Line E |
|---|---|---|---|---|---|---|
| 11 | 2.31 +/- 0.2 | 1.78 +/- 0.09 |  | 1.75 +/- 0.06 | 1.94 +/- 0.07 | 2.05 +/- 0.10 |
| 12 | 2.11 +/- 0.3 | 1.90 +/- 0.07 | 1.97 +/- 0.10 | 1.90 +/- 0.07 | 2.03 +/- 0.06 | 2.03 +/- 0.07 |
| 22 | 2.15 +/- 0.4 | 1.97 +/- 0.06 | 2.00 +/- 0.07 | 1.97 +/- 0.08 | 2.11 +/- 0.06 | 2.08 +/- 0.08 |
|  | P < .84 | P < .14 | P < .56 | P < .14 | P < .01 | P < .36 |

Having described the invention with reference to particular compositions, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. The claims are meant to cover the claimed components and steps in any sequence which is effective to meet the objectives there intended, unless the context specifically indicates to the contrary.

The following citations are hereby incorporated in their entirety by reference:

Andersson L B (1996) "Genes and obesity", *Ann Med.*, 28:5–7.

Arden K C (1990). "The Receptors for Prolactin and Growth Hormone are Localized in the same Region of Human Chromosome 5", *Cytogenet. Cell Genet.* 53:161–165.

Barinaga M (1996). "Researchers Nail Down Leptin Receptor", *Science* 271:913.

Bray G A (1978). *Physiol. Rev.* 59, 719–809.

Casas-Carillo E (1997) "Mapping genomic regions associated with growth rate in pigs", *J Anim Sci* 75:2047–2053.

Chajlani V, "Molecular Cloning of a Novel Human Melanocortin Receptor", *Biochem. Biophys. Res. Commun.*, 195, 866–873.

Chen H (1995). "Evidence that the diabetes gene encodes the leptin receptor: Identification of a mutation in the leptin receptor gene in db/db mice", *Cell* 84, 491–495.

Chevalet C (1996). CABIOS. In Press.

Chua S C (1996). *Science* 271, 994–996.

Chung W K (1996). *Genome Res.* 6, 431–438.

Cioffi J A (1996). *Nature Med.* 2, 585–589.

Cybulsky M I (1991). "Gene Structure, Chromosomal Location, and Basis for Alternative mRNA Splicing of the Human VCAM1 Gene". *Proc. Nat. Acad. Sci.* 88:7859–7863.

Dekkers J C M (1998) "Optimizing selection for quantitative traits with information on an identified locus in outbred population", *Genet Res* 71:257–275.

Flier J S (1998), "Obesity and the hypothalamus: Novel peptides for new pathways", *Cell* 92:437–440.

Frandberg P (1997) "Glutamine$^{235}$ and argine$^{272}$ in human melanocortin 5 receptor determines its low affinity to MSH", *Biochem Biophys Res Commun* 236:489492.

Frankel W N (1996) "Who's afraid of epistasis?" *Nat Genet* 14:371–373.

Gantz I (1993a) "Molecular Cloning of a Novel Melanocortin Receptor", *J. Biol. Chem.* 268, 8246–8250.

Gantz (1993) "Molecular Cloning, Expression in Gene Localization of a Fourth Melanocortin Receptor", *J. Biol. Chem.* 268, 15174–15179.

Gantz (1994) "Molecular Cloning Expression and Characterization of a Fifth Melanocortin Receptor", *Biochem. Biophys. Res. Comm.*, 200, 1214–1220.

Ginrdharan N V (1998) "Animal models of obesity and their usefulness in molecular approach to obesity", *Indian J Med res* 108:225–242.

Gotoda T (1997) "Molecular screening of the human melanocortin-4 receptor gene: identification of a missense variant showing no association with obesity, plasma glucose, or insulin" *Diabetologia* 40:976–979.

Goureau A (1996). *Genomics*. In Press.

Griffon N (1994) "Molecular Cloning and Characterization of the Rat Fifth Melanocortin Receptor", *Biochem. Biophys. Res. Comm.*, 200,1007–1014.

Helm J (1994) "Rapid Communication: SacI Restriction Fragment Length Polymorphism with a Porcine Vascular Cell Adhesion Molecule 1 (VCAM1) cDNA Fragment", *J. Anim. Science* 72:2764.

Hinney A (1999) "Several mutations in the melanocortin-4 receptor gene including a nonsense and a frameshift mutation associated with dominantly inherited obesity in humans" *J Clin Endocrinol Metab* 84:1483–1486.

Huszar (1997) "Targeted disruption of the Melanocortin-4 Receptor Results in/Obesity in Mice", *Cell* 88:131–141.

Kask A (1998) "Evidence that orexigenic effects of melanocortin 4 receptor antagonist HS014 are mediated by neuropeptide Y" *Biochem Biophys Res Commun* 248:245–249.

Kim K S (1999) "Rapid Communication: Linkage and physical mapping of the porcine Melanocortin-4 Receptor (MC4R gene" *J Anim Sci* (submitted).

Knorr C (1997) "Associations of GH gene variants with performance traits in F2 generations of European wild boar, Pietrain and Meishan pigs" *Anim Genet* 28:124–128.

Knott S A (1998) "Multiple marker mapping of quantitative trait loci in a cross between outbred wild boar and large white pigs" *Genetics* 149:1069–1680.

Labbe O (1994) "Molecular Cloning of a Mouse Melanocortin-5 Receptor Gene Widely Expressed in Peripheral Tissues", *Biochemistry* 33, 4543–4549.

Lee G H (1996). *Nature* 379, 632–635.

Lu Dongsi "Agouti Protein is an Antagonist of the Melanocyte-Stimulating Hormone Receptor" *Letters to Nature*.

Marsh D J (1999) "Response of melanocortin-4 receptor-deficient mice to anorectic and orexigenic peptides" *Nat Genet* 21:119–122.

Messer L, (1996a) "Mapping and Investigation of Candidate Genes for Litter Size in French Large White Pigs" *ISAG Proceedings* (submitted).

Messer L (1996b) "Linkage Mapping of the Retinoic Acid Receptor Gamma (RARG) Gene to Porcine Chromosome 5". *Anim. Genet.* (in press).

Messer L (1996c) "Linkage mapping of the Retinol Binding Protein 4 (RBP4) Gene to Porcine Chromosome 14". *Mammal. Genome* (in press).

Meuwissen T H E (1996) "The use of marker haplotypes in animal breeding schemes" *Genet Sel Evol* 28:161–176.

Montjoy K G (1992) "The Cloning of a Family of Genes that Encode the Melanocortin Receptors", *Science* 257, 1248–1251.

Montjoy K G (1994) "Localization of the Melanocortin-4 Receptor (MC4R) In Neuroendocrine In Autonomic Control Circuits in the Brain" *Mol. Endocrinol.* 8, 1298–1308.

Paszek A (1996) "Genomic Scan for Quantitative Trait Loci in Swine." *Proceed. Midwest. ASAS Meeting*, p. 24.

Paszek A A (1999) "Interval mapping of growth in divergent swine cross" *Mamm Genome* 10:117–122.

Phillips M (1996) "Leptin Receptor Missense Mutation in the Fatty Zucker Rat", *Nature Genetics* 13:18–19.

Pomp D (1997) "Genetic dissection of obesity in polygenic animal models" *Behav Genet* 27:285–306.

Robbins L S (1993) "Pigmentation phenotypes of variant extension locus alleles result from point mutations that alter MSH receptor function" *Cell* 72:827–834.

Robic A (1996). *Mamm. Genome* 7,438–445.

Rohrer G A (1998) "Identification of quantitative trait loci affecting carcass composition in swine: I. Fat deposition traits" *J Anim Sci* 76:2247–2254.

Rothschild M F (1996). "The Estrogen Receptor Locus is Associated With a Major Gene for Litter Size in Pigs". *PNAS* 93: 201–205.

Rothschild M F (1999) "Advances in pig genomics and industry applications" *AgBiotechNet* 1:1–8.

Schwartz M W (1999) "Model for the regulation of energy balance and adiposity by the central nervous system" *Am J Clin Nutr* 69:584–96.

Seeley R J (1997) "Melanocortin receptors in leptin effects", *Nature* 390:349.

Tartaglia L A (1995) "Identification and Expression Cloning of a Leptin Receptor" *Cell* 83:1263–1271.

Tatro J B (1996) "Receptor biology of the melanocortins, a family of neuroimmunomodulatory peptides", *Neuroimmunomodulation* 3:259–284.

Truett G E (1995). *Mamm. Genome* 6, 25–30.

Vaisse C (1998) "A frameshift mutation in human MC4R is associated with a dominant form of obesity" *Nat Genet* 20:113–114.

Valverde P (1995) "Variants of the melanocyte-stimulating hormone receptor gene are associated with red hair and fair skin in humans" *Nat Genet* 11:328–330.

Wang L (1998) "A direct search for quantitative trait loci on chromosomes 4 and 7 in pigs" *J Anim Sci* 76:2560–2567.

Warner C M (1991). "The Swine Major Histocompatibility Complex (SLA)" in *Immunogenetics of the MHC*, VCH Publishers, NY, N.Y., pp. 368–397.

Winick J D (1996). *Genomics* 36, 221–222.

Xy Y (1994) "Identification of the Ped Gene at the Molecular Level: The Q9 MHC Class I Transgene Converts the Ped Slow Phenotype to Ped Fast Phenotype" *Biol. Reprod.* 51:695–699.

Yeo G S (1998) "A frameshift mutation in MC4R associated with dominantly inherited human obesity" *Nat Genet* 20:111–112.

Yerle M (1996). *Cytozenet. Cell Genet.* 73, 194–202.

Youngs C R (1993) "Investigation into the Control of Litter Size in Swine: I. Comparative Studies on in vitro Development of Meishan and Yorkshire Preimplantation Embryos" *J. Anim. Sci.*, 1561–1565.

Yu T P (1995) "Association of PIT1 polymorphisms with growth and carcass traits in pigs" *J Anim Sci* 73:1282–1288.

Zhang Y (1994) "Positional cloning of the mouse obese gene and its human homologue", *Nature* 372:425–432.

Ziang Z H (1999) "Genetic polymorphisms in the leptin gene and their association with fatness in four pig breeds" *Mamin Genome* 12:191–193.

What is claimed is:

1. A method for identifying a pig with a polymorphism at position 678 SEQ ID NO:1, wherein a pig with a guanine at position 678 is indicative of said pig more likely to have less back fat, lower daily gain, and lower feed intake than a pig with an adenine at position 678 of SEQ ID NO:1, wherein an adenine is indicative of higher feed intake the method comprising:

detecting the nucleotide present at position 678 of SEQ ID NO: 1; and
   relating the polymorphism to the phenotype.

2. The method of claim 1 wherein the polymorphism is detected at position 678 of a PCR sequence using a forward primer and a reverse primer.

3. The method of claim 1 wherein the step of detecting the polymorphism is a method employing allele specific oligonucleotides.

4. The method of claim 1 wherein the step of detecting the polymorphism is selected from the group consisting of restriction fragment length polymorphism (RFLP) analysis, heteroduplex analysis, single strand conformational polymorphism (SSCP) analysis, denaturing gradient gel electrophoresis (DGGE), and temperature gradient gel electrophoresis (TGGE).

5. The method of claim 4 wherein the step of detecting the polymorphism comprises RFLP analysis.

6. The method of claim 1 further comprising the step of amplifying SEQ ID NO:1 or a region of thereof containing said polymorphism.

7. The method of claim 6 further comprising the step of digesting the amplified region with the restriction endonuclease Taq I.

8. A method of identifying a pig which possesses an allele of a polymorphism at the codon encoding amino acid 298 of the melanocortin-4-receptor protein, said amino acid being in the seventh transmembrane domain of the protein, said method comprising:

obtaining a nucleic acid sample from a pig and identifying the encoded amino acid within the translated MC4R protein, wherein an encoded aspartic acid at amino acid 298 identifies leanness and lower feed intake than pigs with an encoded asparagine at amino acid 298 and an encoded asparagine at amino acid-298 identifies a faster rate of gain than pigs with an encoded aspartic acid at position 298 of the MC4R protein.

9. The method of claim 6 wherein the forward primer is SEQ ID NO: 5 and the reverse primer is SEQ ID NO: 6.

10. The method of claim 6 wherein the forward primer is SEQ ID NO: 7 the reverse primer is SEQ ID NO: 8.

11. The method of claim 6 wherein the forward primer is SEQ ID NO: 9 and the reverse primer is SEQ ID NO: 10.

* * * * *

SEQUENCE LISTING

<160> NUMBER OF SEQ ID NOS: 30

<210> SEQ ID NO 1
<211> LENGTH: 746
<212> TYPE: DNA
<213> ORGANISM: Sus scrofa
<220> FEATURE:
<221> NAME/KEY: variation
<222> LOCATION: (678)..(678)
<223> OTHER INFORMATION: G/A

<400> SEQUENCE: 1

```
acaagaatct gcattcaccc atgtactttt tcatctgtag cctggctgtg gctgatatgc        60
tggtgagcgt ttccaatggg tcagaaacca ttgtcatcac cctattaaac agcacggaca       120
cggacgcaca gagtttcaca gtgaatattg ataatgtcat tgactcagtg atctgtagct       180
ccttactcgc ctcaatttgc agcctgcttt cgattgcagt ggacaggtat tttactatct       240
tttatgctct ccagtaccat aacattatga cagttaagcg ggttggaatc atcatcagtt       300
gtatctgggc agtctgcacg gtgtcgggtg ttttgttcat catttactca gatagcagtg       360
ctgttattat ctgcctcata accgtgttct tcaccatgct ggctctcatg gcttctctct       420
atgtccacat gttcctcatg gccagactcc acattaagag gatcgccgtc ctcccaggca       480
ctggcaccat ccgccaaggt gccaacatga aggggggcaat taccctgacc atcttgattg      540
gggtctttgt ggtctgctgg gccccttct tcctccactt aatattctat atctcctgcc       600
cccagaatcc atactgtgtg tgcttcatgt ctcactttaa tttgtatctc atcctgatca       660
tgtgtaattc catcatcrat cccctgattt atgcactccg gagccaagaa ctgaggaaaa       720
ccttcaaaga gatcatctgt tgctat                                             746
```

<210> SEQ ID NO 2
<211> LENGTH: 840
<212> TYPE: DNA
<213> ORGANISM: Homo sapiens

<400> SEQUENCE: 2

```
atatcttagt gattgtggca atagccaaga acaagaatct gcattcaccc atgtactttt        60
tcatctgcag cttggctgtg gctgatatgc tggtgagcgt ttcaaatgga tcagaaacca       120
ttatcatcac cctattaaac agtacagata cggatgcaca gagtttcaca gtgaatattg       180
ataatgtcat tgactcggtg atctgtagct ccttgcttgc atccatttgc agcctgcttt       240
caattgcagt ggacaggtac tttactatct tctatgctct ccagtaccat aacattatga       300
cagttaagcg ggttgggatc agcataagtt gtatctgggc agcttgcacg gtttcaggca       360
ttttgttcat catttactca gatagtagtg ctgtcatcat ctgcctcatc accatgttct       420
tcaccatgct ggctctcatg gcttctctct atgtccacat gttcctgatg gccaggcttc       480
acattaagag gattgctgtc ctccccggca ctggtgccat ccgccaaggt gccaatatga       540
agggagcgat taccttgacc atcctgattg gcgtctttgt tgtctgctgg gccccattct       600
tcctccactt aatattctac atctcttgtc ctcagaatcc atattgtgtg tgcttcatgt       660
```

```
ctcactttaa cttgtatctc atactgatca tgtgtaattc aatcatcgat cctctgattt    720
atgcactccg gagtcaagaa ctgaggaaaa ccttcaaaga gatcatctgt tgctatcccc    780
tgggaggcct ttgtgacttg tctagcagat attaaatggg gacagagcac gcaatatagg    840
```

<210> SEQ ID NO 3
<211> LENGTH: 311
<212> TYPE: PRT
<213> ORGANISM: Homo sapiens
<220> FEATURE:
<221> NAME/KEY: misc_feature
<222> LOCATION: (298)..(298)
<223> OTHER INFORMATION: "X" can be any amino acid

<400> SEQUENCE: 3

```
Gln Leu Phe Val Ser Pro Glu Val Phe Val Thr Leu Gly Val Ile Ser
1               5                  10                  15

Leu Leu Glu Asn Ile Leu Val Ile Val Ala Ile Ala Lys Asn Lys Asn
            20                  25                  30

Leu His Ser Pro Met Tyr Phe Phe Ile Cys Ser Leu Ala Val Ala Asp
        35                  40                  45

Met Leu Val Ser Val Ser Asn Gly Ser Glu Thr Ile Ile Thr Leu
    50                  55                  60

Leu Asn Ser Thr Asp Thr Asp Ala Gln Ser Phe Thr Val Asn Ile Asp
65                  70                  75                  80

Asn Val Ile Asp Ser Val Ile Cys Ser Ser Leu Leu Ala Ser Ile Cys
                85                  90                  95

Ser Leu Leu Ser Ile Ala Val Asp Arg Tyr Phe Thr Ile Phe Tyr Ala
            100                 105                 110

Leu Gln Tyr His Asn Ile Met Thr Val Lys Arg Val Gly Ile Ser Ile
        115                 120                 125

Ser Cys Ile Trp Ala Ala Cys Thr Val Ser Gly Ile Leu Phe Ile Ile
    130                 135                 140

Tyr Ser Asp Ser Ser Ala Val Ile Ile Cys Leu Ile Thr Met Phe Phe
145                 150                 155                 160

Thr Met Leu Ala Leu Met Ala Ser Leu Tyr Val His Met Phe Leu Met
                165                 170                 175

Ala Arg Leu His Ile Lys Arg Ile Ala Val Leu Pro Gly Thr Gly Ala
            180                 185                 190

Ile Arg Gln Gly Ala Asn Met Lys Gly Ala Ile Thr Leu Thr Ile Leu
        195                 200                 205

Ile Gly Val Phe Val Val Cys Trp Ala Pro Phe Phe Leu His Leu Ile
    210                 215                 220

Phe Tyr Ile Ser Cys Pro Gln Asn Pro Tyr Cys Val Cys Phe Met Ser
225                 230                 235                 240

His Phe Asn Leu Tyr Leu Ile Leu Ile Met Cys Asn Ser Ile Ile Asp
                245                 250                 255

Pro Leu Ile Tyr Ala Leu Arg Ser Gln Glu Leu Arg Lys Thr Phe Lys
            260                 265                 270

Glu Ile Ile Cys Cys Tyr Pro Leu Gly Gly Leu Cys Asp Leu Ser Ser
        275                 280                 285

Arg Tyr Ala Pro Pro Glu Asn Asp Ile Xaa Val Ile Cys Asn Phe Ile
    290                 295                 300

Asp Glu Asn Thr Ile Ala Leu
305                 310
```

<210> SEQ ID NO 4
<211> LENGTH: 248
<212> TYPE: PRT
<213> ORGANISM: Sus scrofa

<400> SEQUENCE: 4

```
Lys Asn Leu His Ser Pro Met Tyr Phe Phe Ile Cys Ser Leu Ala Val
1               5                   10                  15

Ala Asp Met Leu Val Ser Val Ser Asn Gly Ser Glu Thr Ile Val Ile
            20                  25                  30

Thr Leu Leu Asn Ser Thr Asp Thr Asp Ala Gln Ser Phe Thr Val Asn
        35                  40                  45

Ile Asp Asn Val Ile Asp Ser Val Ile Cys Ser Ser Leu Leu Ala Ser
50                  55                  60

Ile Cys Ser Leu Leu Ser Ile Ala Val Asp Arg Tyr Phe Thr Ile Phe
65                  70                  75                  80

Tyr Ala Leu Gln Tyr His Asn Ile Met Thr Val Lys Arg Val Gly Ile
                85                  90                  95

Ile Ile Ser Cys Ile Trp Ala Val Cys Thr Val Ser Gly Val Leu Phe
            100                 105                 110

Ile Ile Tyr Ser Asp Ser Ser Ala Val Ile Ile Cys Leu Ile Thr Val
        115                 120                 125

Phe Phe Thr Met Leu Ala Leu Met Ala Ser Leu Tyr Val His Met Phe
130                 135                 140

Leu Met Ala Arg Leu His Ile Lys Arg Ile Ala Val Leu Pro Gly Thr
145                 150                 155                 160

Gly Thr Ile Arg Gln Gly Ala Asn Met Lys Gly Ala Ile Thr Leu Thr
                165                 170                 175

Ile Leu Ile Gly Val Phe Val Val Cys Trp Ala Pro Phe Phe Leu His
            180                 185                 190

Leu Ile Phe Tyr Ile Ser Cys Pro Gln Asn Pro Tyr Cys Val Cys Phe
        195                 200                 205

Met Ser His Phe Asn Leu Tyr Leu Ile Leu Ile Met Cys Asn Ser Ile
210                 215                 220

Ile Asn Pro Leu Ile Tyr Ala Leu Arg Ser Gln Glu Leu Arg Lys Thr
225                 230                 235                 240

Phe Lys Glu Ile Ile Cys Cys Tyr
                245
```

<210> SEQ ID NO 5
<211> LENGTH: 20
<212> TYPE: DNA
<213> ORGANISM: Sus scrofa

<400> SEQUENCE: 5
tggcaatagc caagaacaag                                            20

<210> SEQ ID NO 6
<211> LENGTH: 20
<212> TYPE: DNA
<213> ORGANISM: Sus scrofa

<400> SEQUENCE: 6 cagggatag caacagatga                                             20

<210> SEQ ID NO 7
<211> LENGTH: 18

```
<212> TYPE: DNA
<213> ORGANISM: Sus scrofa

<400> SEQUENCE: 7
ttaagtggag gaagaagg                                              18

<210> SEQ ID NO 8
<211> LENGTH: 19
<212> TYPE: DNA
<213> ORGANISM: Sus scrofa

<400> SEQUENCE: 8
cattatgaca gttaagcgg                                             19

<210> SEQ ID NO 9
<211> LENGTH: 20
<212> TYPE: DNA
<213> ORGANISM: Sus scrofa

<400> SEQUENCE: 9
taccctgacc atcttgattg                                            20

<210> SEQ ID NO 10
<211> LENGTH: 22
<212> TYPE: DNA
<213> ORGANISM: Sus scrofa

<400> SEQUENCE: 10
atagcaacag atgatctctt tg                                         22

<210> SEQ ID NO 11
<211> LENGTH: 24
<212> TYPE: PRT
<213> ORGANISM: Sus scrofa

<400> SEQUENCE: 11

Met Ser His Phe Asn Leu Tyr Leu Ile Leu Ile Met Cys Asn Ser Ile
 1               5                  10                  15

Ile Asp Pro Leu Ile Tyr Ala Leu
             20

<210> SEQ ID NO 12
<211> LENGTH: 24
<212> TYPE: PRT
<213> ORGANISM: Homo sapiens

<400> SEQUENCE: 12

Met Ser His Phe Asn Leu Tyr Leu Ile Leu Ile Met Cys Asn Ser Ile
 1               5                  10                  15

Ile Asp Pro Leu Ile Tyr Ala Leu
             20

<210> SEQ ID NO 13
<211> LENGTH: 24
<212> TYPE: PRT
<213> ORGANISM: Rattus norvegicus

<400> SEQUENCE: 13

Met Ser His Phe Asn Leu Tyr Leu Ile Leu Ile Met Cys Asn Ala Val
 1               5                  10                  15

Ile Asp Pro Leu Ile Tyr Ala Leu
             20
```

```
<210> SEQ ID NO 14
<211> LENGTH: 23
<212> TYPE: PRT
<213> ORGANISM: Ovis aries

<400> SEQUENCE: 14

Met Ser His Phe Asn Met Tyr Leu Ile Leu Ile Met Cys Asn Ser Val
1               5                   10                  15

Ile Asp Pro Leu Ile Tyr Ala
            20

<210> SEQ ID NO 15
<211> LENGTH: 23
<212> TYPE: PRT
<213> ORGANISM: Bos taurus

<400> SEQUENCE: 15

Met Ser His Phe Asn Met Tyr Leu Ile Leu Ile Met Cys Asn Ser Val
1               5                   10                  15

Ile Asp Pro Leu Ile Tyr Ala
            20

<210> SEQ ID NO 16
<211> LENGTH: 24
<212> TYPE: PRT
<213> ORGANISM: Bos taurus

<400> SEQUENCE: 16

Met Ser Leu Phe Gln Val Asn Gly Val Leu Ile Met Cys Asn Ala Ile
1               5                   10                  15

Ile Asp Pro Phe Ile Tyr Ala Leu
            20

<210> SEQ ID NO 17
<211> LENGTH: 22
<212> TYPE: PRT
<213> ORGANISM: Homo sapiens

<400> SEQUENCE: 17

Ala His Phe Asn Thr Tyr Leu Val Leu Ile Met Cys Asn Ser Val Ile
1               5                   10                  15

Asp Pro Leu Ile Tyr Ala
            20

<210> SEQ ID NO 18
<211> LENGTH: 22
<212> TYPE: PRT
<213> ORGANISM: Mus musculus

<400> SEQUENCE: 18

Ala His Phe Asn Thr Tyr Leu Val Leu Ile Met Cys Asn Ser Val Ile
1               5                   10                  15

Asp Pro Leu Ile Tyr Ala
            20

<210> SEQ ID NO 19
<211> LENGTH: 23
<212> TYPE: PRT
<213> ORGANISM: Homo sapiens

<400> SEQUENCE: 19

Met Ser His Phe Asn Met Tyr Leu Ile Leu Ile Met Cys Asn Ser Val
```

```
                1               5              10              15

Met Asp Pro Leu Ile Tyr Ala
             20

<210> SEQ ID NO 20
<211> LENGTH: 22
<212> TYPE: PRT
<213> ORGANISM: Homo sapiens

<400> SEQUENCE: 20

Ser Tyr Phe Asn Leu Phe Leu Ile Leu Ile Cys Asn Ser Val Val
1               5              10              15

Asp Pro Leu Ile Tyr Ala
             20

<210> SEQ ID NO 21
<211> LENGTH: 25
<212> TYPE: PRT
<213> ORGANISM: Bos taurus

<400> SEQUENCE: 21

Leu Ala Tyr Glu Lys Phe Phe Leu Leu Leu Ala Glu Phe Asn Ser Ala
1               5              10              15

Met Asn Pro Ile Ile Tyr Ser Tyr Arg
             20                  25

<210> SEQ ID NO 22
<211> LENGTH: 19
<212> TYPE: PRT
<213> ORGANISM: Homo sapiens

<400> SEQUENCE: 22

Phe Leu Leu Leu Ala Glu Ala Asn Ser Leu Val Asn Ala Ala Val Tyr
1               5              10              15

Ser Cys Arg

<210> SEQ ID NO 23
<211> LENGTH: 22
<212> TYPE: PRT
<213> ORGANISM: Homo sapiens

<400> SEQUENCE: 23

Val Phe Ala Phe Cys Ser Met Leu Cys Leu Leu Asn Ser Thr Val Asn
1               5              10              15

Pro Leu Ile Tyr Ala Leu
             20

<210> SEQ ID NO 24
<211> LENGTH: 21
<212> TYPE: PRT
<213> ORGANISM: Homo sapiens

<400> SEQUENCE: 24

Phe Gln Phe Phe Phe Trp Ile Gly Tyr Cys Asn Ser Ser Leu Asn Pro
1               5              10              15

Val Ile Tyr Thr Ile
             20

<210> SEQ ID NO 25
<211> LENGTH: 22
<212> TYPE: PRT
<213> ORGANISM: Rattus norvegicus
```

-continued

```
<400> SEQUENCE: 25

Phe Asp Phe Val Val Ile Leu Thr Tyr Ala Asn Ser Cys Ala Asn Pro
1               5                   10                  15

Ile Leu Tyr Ala Phe Leu
            20

<210> SEQ ID NO 26
<211> LENGTH: 16
<212> TYPE: PRT
<213> ORGANISM: Homo sapiens

<400> SEQUENCE: 26

Leu Ala Tyr Ser Asn Ser Ser Val Asn Pro Ile Ile Tyr Ala Phe Leu
1               5                   10                  15

<210> SEQ ID NO 27
<211> LENGTH: 30
<212> TYPE: DNA
<213> ORGANISM: Sus scrofa

<400> SEQUENCE: 27
gtgtaattcc atcatcgatc ccctgattta                                    30

<210> SEQ ID NO 28
<211> LENGTH: 30
<212> TYPE: DNA
<213> ORGANISM: Sus scrofa

<400> SEQUENCE: 28
gtgtaattcc atcatcaatc ccctgattta                                    30

<210> SEQ ID NO 29
<211> LENGTH: 10
<212> TYPE: PRT
<213> ORGANISM: Sus scrofa

<400> SEQUENCE: 29

Cys Asn Ser Leu Ile Asp Pro Leu Ile Tyr
1               5                   10

<210> SEQ ID NO 30
<211> LENGTH: 10
<212> TYPE: PRT
<213> ORGANISM: Sus scrofa

<400> SEQUENCE: 30

Cys Asn Ser Leu Ile Asn Pro Leu Ile Tyr
1               5                   10
6
```